United States Patent [19]

Vallhonrat

[11] 4,194,290

[45] Mar. 25, 1980

[54] BUCCAL HYGIENIC INSTRUMENT

[76] Inventor: Orlando D. Vallhonrat, 8461 SW. 84 Ter., Miami, Fla. 33143

[21] Appl. No.: 890,636

[22] Filed: Mar. 20, 1978

[51] Int. Cl.² ............................................... A61C 15/00
[52] U.S. Cl. ...................................... 433/141; 132/89; 132/91; 132/84 R; 433/80
[58] Field of Search ........... 32/40 R; 132/84 R, 84 A, 132/89, 92 A, 91; 15/167, 110

[56] References Cited

U.S. PATENT DOCUMENTS

| | | | |
|---|---|---|---|
| 1,537,853 | 5/1925 | Mason | 132/84 A |
| 1,816,092 | 7/1931 | Schmitter | 132/84 A |
| 2,798,241 | 7/1957 | Cohen | 132/84 R |
| 3,902,509 | 9/1975 | Tundermann et al. | 132/84 R |
| 4,041,962 | 8/1977 | Johansson et al. | 132/91 |

*Primary Examiner*—Louis G. Mancene
*Assistant Examiner*—Michael J. Foycik, Jr.

[57] ABSTRACT

A hygienic instrument of a disposable type for use in cleaning surfaces within a person's mouth which is composed of a elongate member having a pointed end for picking the teeth and an opposite end with a foam pad or brush impregnated with a cleaning substance and including two laterally extending pegs spanned by a strand of dental floss, the laterally extending pegs being intermediate the length of the elongate member.

9 Claims, 6 Drawing Figures

BUCCAL HYGIENIC INSTRUMENT

FIELD OF THE INVENTION

This invention relates to hygienic instruments and, more particularly, to a hygienic instrument which is disposable and is for use in cleaning the surfaces in the mouth.

BACKGROUND OF THE INVENTION

In the past there have been numerous types of devices which have been utilized for cleaning teeth and which fall into the category of toothpicks, toothbrushes, and dental floss. Oftentimes these devices have constituted a combination device to perform two functions. This invention is of a hygienic instrument for cleaning the surfaces in the mouth which comprises three functions, picking debris from the teeth, scrubbing the teeth with an affixed pad or brush impregnated with cleansing material and using dental floss to remove materials between the teeth. Prior art devices are shown in U.S. Pat. No. 3,698,405 for a Orthodontal Toothpick, U.S. Pat. No. 1,695,238 for a Tooth Cleaner, U.S. Pat. No. 3,533,420 for a Dental Floss Holder; U.S. Pat. No. 3,775,848 for a Periodontal and Dental Cleanser and Periodontal Stimulator; U.S. Pat. No. 3,094,996 for a Dental Floss Holder and Applicator; U.S. Pat. No. 2,931,370 for a Combined Condiment Holder and Toothpick; and U.S. Pat. No. 3,621,853 for a Dental Floss Holding Device.

OBJECTS OF THE PRESENT INVENTION

It is an object of the present invention to provide a disposable, lightweight inexpensive, practical buccal hygienic instrument which is ideal to be dispensed from machines or given away in restaurants, dining rooms, schools, factories, offices, or to dining guests at homes, etc., where eating takes place or which may be sold in a blister type package and which is also useful for persons on picnics, when boating or camping. The device may additionally be used by airlines and served with the meal for use following the meal with a little water and which device is composed of an elongate member having a pointed end for picking the teeth and an opposite end with a pad or brush affixed to it which may be impregnated with a cleansing material and wherein dental floss pegs extend laterally from the intermediate zone of the member and these pegs are spanned by dental floss for use in cleaning the teeth.

In accordance with the foregoing objects, the instant invention will now be described with reference to the accompanying drawings in which:

DESCRIPTION OF THE PREFERRED EMBODIMENT

Figure 1:
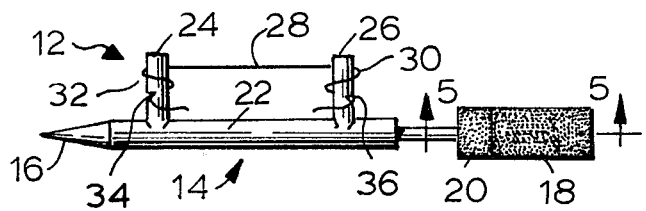
FIG. 1 is a side elevation view of the instant invention.

Referring to the drawings wherein like reference characters designate like or corresponding parts throughout the several views, the instrument is generally designated by the numeral 12 and it is seen to be composed of an elongate member 14 having a pointed end 16 and an opposite end 18 to which there is applied a cleansing means in the form of a foam pad in the preferred illustrated embodiment of a brush which is, preferably, impregnated with a cleansing material. From the intermediate zone 22 there extend laterally two pegs 24 and 26 which are spanned by a strand of dental floss 28 having ends 30 and 32 which are wrapped about the pad or brush and which may be secured in notches 34 and 36 so that the dental floss is taut. The scouring pad may be provided with an elongate recess as at 40 and the end 18 of the member may be dipped in adhesive to coat it as at 42 to secure it firmly to the end of the member 14. The impregnation of the pad or brush may be by suitable means, by dipping, soaking, or otherwise injecting cleansing material, such as toothpaste, tooth cleaning material such as a tooth powder, or a soapy type cleansing material suitable for use in tooth cleansing.

Figure 2:
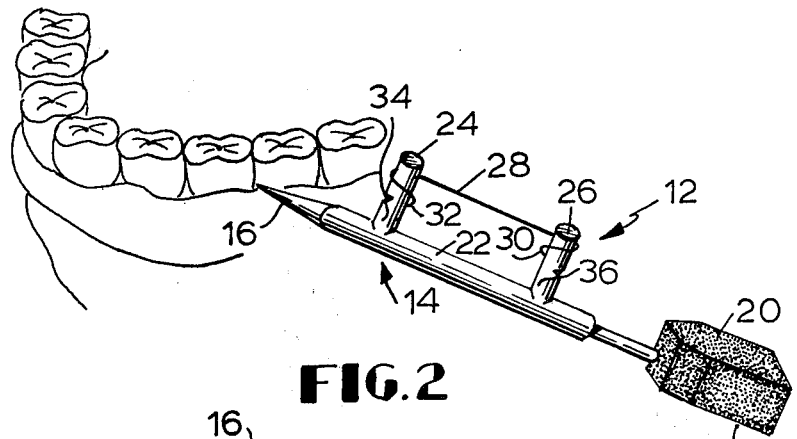
FIG. 2 is a view similar to FIG. 1 and illustrating the use of the instant invention for picking teeth.
Figure 3:
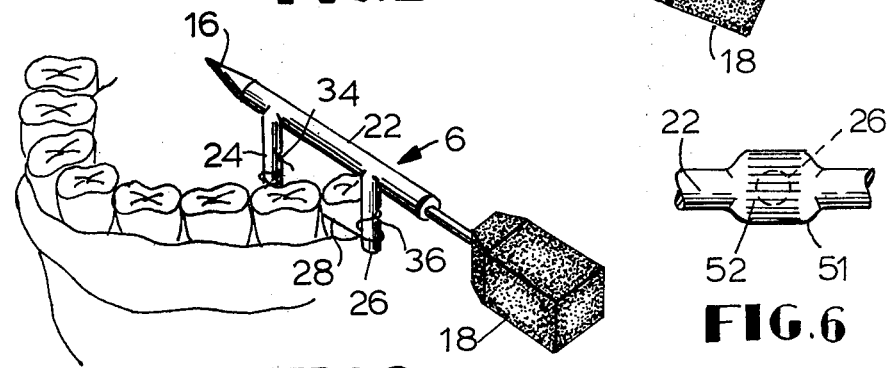
FIG. 3 is a view similar to FIG. 2 and illustrating the instant invention in use with dental floss.
Figure 4:
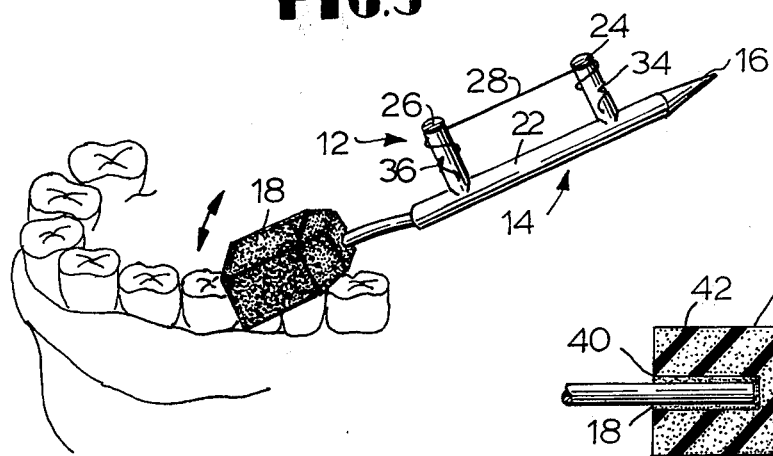
FIG. 4 is a view similar to FIGS. 2 and 3 and illustrating the use of the device for cleaning the teeth.
Figure 5:
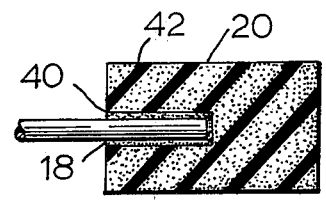
FIG. 5 is a view in cross section of the pad or brush and of the device shown in FIG. 5 taken on the plane indicated by the line 5—5 and looking in the direction of the arrows.

In use, the pointed end 16 is adapted to be used to pick teeth as shown in FIG. 2 while a dental floss is adapted to be used as shown in FIG. 3, and a scouring or cleansing takes place by rubbing action as shown in FIG. 4.

Figure 6:
FIG. 6 is an enlarged view of the zone designated by the numeral 6 in FIG. 3 and illustrating a gripping zone, which may be embodied in an alternative embodiment.

The device may have a gripper zone intermediate the ends, such as is indicated in FIG. 6 wherein the intermediate zone 22 is provided with an enlarged outer surface at about the juncture of the peg 26, shown in dotted lines and wherein the enlarged portion designated by the numeral 51 is provided with exterior score marks 52 for manipulating the hygienic instrument.

What is claimed is:

1. A disposable buccal hygienic instrument comprising an elongate member having a pointed first end comprising a toothpick and an opposite second end, said elongate member including an intermediate zone and a laterally extending peg on the intermediate zone spaced from and adjacent the pointed end and another laterally extending peg on the intermediate zone adjacent the second end and each of said pegs being spanned by a strand of dental floss and means securing the ends of the dental floss to the pegs in spanning relation thereof; and a cleansing means fixed to the second end completely covering the same and said cleansing means including cleansing material.

2. The device as set forth in claim 1 wherein the cleansing means comprises a pad of foam material.

3. The device as set forth in claim 1 wherein said cleansing means comprises foam material.

4. The device as set forth in claim 3 wherein said foam material is fixed to the second end by glue means.

5. The device as set forth in claim 2 wherein the cleansing material is of a powder impregnated in the foam material.

6. The device as set forth in claim 1 wherein the pegs include recesses intermediate the lengths thereof and adjacent the elongate member to secure dental floss therein.

7. The instrument as set forth in claim 1 wherein an enlarged gripper zone is provided intermediate said ends for manipulating said instrument.

8. The instrument as set forth in claim 7 wherein said gripper means comprises an enlarged zone with a pattern in relief on the surface thereof providing a gripping surface.

9. The instrument as set forth in claim 1 wherein said cleansing means comprises brush means.

* * * * *